United States Patent
Boshra et al.

(10) Patent No.: US 9,416,082 B2
(45) Date of Patent: Aug. 16, 2016

(54) PROCESS FOR THE ISOMERISATION OF AN EXO DOUBLE BOND

(71) Applicant: FIRMENICH SA, Geneva (CH)

(72) Inventors: Ramez Boshra, Newark, NJ (US);
Koenraad Vanhessche, Feigeres (FR);
Anatoly Alexander, Newark, NJ (US)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/768,222

(22) PCT Filed: Feb. 7, 2014

(86) PCT No.: PCT/EP2014/052432
§ 371 (c)(1),
(2) Date: Aug. 15, 2015

(87) PCT Pub. No.: WO2014/122263
PCT Pub. Date: Aug. 14, 2014

(65) Prior Publication Data
US 2016/0060200 A1 Mar. 3, 2016

Related U.S. Application Data

(60) Provisional application No. 61/763,188, filed on Feb. 11, 2013.

(30) Foreign Application Priority Data

Feb. 25, 2013 (EP) ..................................... 13156519

(51) Int. Cl.
*C07C 45/67* (2006.01)

(52) U.S. Cl.
CPC ............ *C07C 45/67* (2013.01); *C07C 2101/10* (2013.01); *C07C 2101/14* (2013.01)

(58) Field of Classification Search
CPC .. C07C 45/67; C07C 2101/10; C07C 2101/16
USPC .................................. 568/341, 401, 450, 459
See application file for complete search history.

(56) References Cited

U.S. PATENT DOCUMENTS

2008/0009486 A1 1/2008 Chen et al.
2011/0040127 A1* 2/2011 Matsumoto .............. B01J 37/18
568/341

FOREIGN PATENT DOCUMENTS

EP 2266943 12/2010
EP 2269971 1/2011

OTHER PUBLICATIONS

International Search Report and Written Opinion, application PCT/EP2014/052432, mailed Apr. 29, 2014.
Boudjouk et al., Journ. of Catal., 1983, vol. 79, n° 2, 489-492.
Ioffe et al., Chem. of Heteroc. Comp., 1970, vol. 6, 1166-1171.
Perfume and Flavor Chemicals, 1969, Montclair, New Jersey, USA, N° 1956.
Smith M. B. et al., March's Adv. Org. Chem. 5th Ed. NY, Wiley, 2001, pp. 1218-1223.

* cited by examiner

*Primary Examiner* — Sikarl Witherspoon
(74) *Attorney, Agent, or Firm* — Winston & Strawn LLP

(57) ABSTRACT

The present invention concerns a process for the isomerization of an exo double bond toward an endo double bond being performed in the presence of a catalyst system comprising palladium (Pd) or platinum (Pt) and molecular hydrogen or a hydrogen source.

16 Claims, No Drawings

PROCESS FOR THE ISOMERISATION OF AN EXO DOUBLE BOND

TECHNICAL FIELD

The present invention relates to the field of organic synthesis and more specifically it concerns a process for the isomerisation of the exo double bond of compound of formula (I) catalyzed by palladium (Pd) or platinum (Pt) catalyst in the presence of molecular hydrogen or a hydrogen source.

PRIOR ART

Many α,β-unsaturated carbonyl derivatives as defined in formula (I) are useful products as such or useful intermediates of the preparation of other important raw materials. The compounds of formula (I) are of particular interest to the perfumery industry, and in particular 2,3-dimethylbut-2-enal, 2-methylpentadienal or 2-Et-6,6-dimethylcyclohex-2-enone. The first compound is potentially an important intermediate for the preparation of industrially relevant compounds such as 3-methyl citral (3,6,7-Trimethyl-2,6-octadienal; Perfume and Flavor Chemicals, 1969, Montclair, N.J., USA, N° 1956).

However, the preparation of compounds (I) reported in the literature is quite complex and not necessarily very productive (high output). For example, preparation of 2,3-dimethylbut-2-enal has been reported in US2008/0009486 by a reduction of ethyl 2,3-dimethylbut-2-enoate in 2,3-dimethylbut-2-enol and oxidation of the latter by DMSO into the aldehyde. Such approach is quite long, time consuming and has a low productivity.

The preparation of compounds of formula (I) by isomerisation of a compound of formula (II), as presently described, is theoretically very appealing since the starting material is of easy access from aldol reaction with an α-unbranched aldehyde/ketone. However, in order to be effective, especially for an industrial use, such isomerisation needs first an effective catalytic system and second that said catalytic system is able to provide high productivity and selectivity.

There is still a need for a process of isomerisation, as described, having the highest productivity, selectivity and yield.

DESCRIPTION OF THE INVENTION

We have now found that the derivatives of formula (I) can be produced in an advantageous manner by means of a catalytic isomerisation as described and result in minimal byproduct formation and high productivity.

Therefore, a first object of the present invention is a process for the preparation of a compound of formula (I)

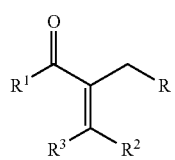

(I)

wherein R, R$^1$ and R$^2$, simultaneously or independently, represent a hydrogen atom or a C$_{1-5}$ alkyl group; R$^3$ represents a C$_{1-5}$ alkyl or alkenyl group; or R$^1$ and R$^3$, taken together, represent a C$_{3-9}$ alkanediyl group optionally substituted by one to two C$_{1-5}$ alkyl groups;

by the isomerisation of the corresponding compound of the formula (II)

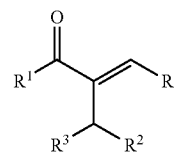

(II)

wherein R, R$^1$, R$^2$ and R$^3$ have the same meaning as in formula (I);
said isomerisation being performed in the presence of a catalyst system comprising
i) metal selected amongst palladium (Pd$^0$) or platinum (Pt$^0$);
ii) molecular hydrogen or a hydrogen source.

For the sake of clarity, it is understood that by the expression "hydrogen source" it is intended the usual meaning in the art, i.e. a compound capable of producing molecular hydrogen (i.e. H$_2$), hydrogen atom or the equivalent in the reaction medium.

The compounds (I) and (II) have at least one carbon-carbon double bonds which can have different stereochemistry (i.e. can be in a E or Z configuration). The said carbon-carbon double bond of said compounds can be in a configuration Z or E or a mixture thereof, or in other words the carbon-carbon double bond can be in the form of an essentially pure isomer (i.e. the (2E) or the (2Z) one) or in the form of a mixture of isomers, e.g. a mixture comprising the isomers (2E) and (2Z) in various w/w ratios.

For the sake of clarity, the alkyl group can be a linear group or a branched group or a cyclic group (for alkyl group having at least 3 carbons).

According to any one of the above embodiments of the invention, said R represents a hydrogen atom or a linear C$_{1-5}$ alkyl group.

According to any one of the above embodiments of the invention, said R$^1$ represents a hydrogen atom.

According to any one of the above embodiments of the invention, said R$^2$ represents hydrogen atom or C$_{1-5}$ alkyl group.

According to any one of the above embodiments of the invention, said R$^3$ represents a linear or branched C$_{1-5}$ alkyl or alkenyl group.

According to any one of the above embodiments of the invention, said R$^1$ and R$^3$, taken together, represent a C$_{3-5}$ alkanediyl substituted by one to two linear or branched C$_{1-3}$ alkyl groups.

According to any one of the above embodiments of the invention, said R$^2$ represents a C$_{1-5}$ alkyl group and said R represents a hydrogen atom.

According to any one of the above embodiments of the invention, the compound of formula (I) is 2-ethyl-6,6-dimethylcyclohex-2-enone and the corresponding compound (II) is 6-ethylidene-2,2-dimethylcyclohexanone or the compound of formula (I) is 2,3-dimethylbut-2-enal and the corresponding compound (II) is 3-methyl-2-methylenebutanal, or the compound of formula (I) is 2-methylpenta-2,4-dienal and the corresponding compound (II) is 2-methylenepent-4-enal.

The compounds of formula (II) are known compounds and can be obtained according to the literature for instance by reacting the aldehyde of formula (III) with compound of formula (IV) (SMITH Michael B., MARCH Jerry, March's Advanced Organic Chemistry 5$^{th}$ Edition. New York: Wiley, 2001, pages 1218-1223)

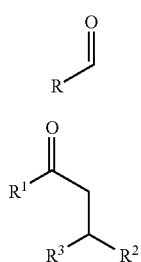

(III)

(IV)

The invention's process is carried out in the presence of a catalytic amount of palladium ($Pd^0$) or platinum ($Pt^0$) in elemental metallic form. Suitable forms of such metal for carrying out chemical reactions are well known to a person skilled in the art.

According to any one of the above embodiments of the invention, said palladium ($Pd^0$) or platinum ($Pt^0$) is supported on a carrying material.

For the sake of clarity, by carrying material it is intended a material wherein it is possible to deposit such metal and which is inert toward the hydrogen source and the substrate.

According to any one of the above embodiments of the invention, specific and non limiting examples of carrying material is carbon or aluminum oxide. Such supports are well known to a person skilled in the art.

The supported palladium ($Pd^0$) or platinum ($Pt^0$) are known compounds and are commercially available. A person skilled in the art is able to select the preferred kind of metal as the way that it was deposit on the support, as the proportion of metal on support material, as the form (powder, granules, pellets, extrudates, mousses . . . ) and as the surface area of the support.

According to any one of the above embodiments of the invention, the amount of metal relative to the support can range between 0.5% and 10% w/w, or even between 1% and 6%, relative to the weight on the support used.

The palladium ($Pd^0$) or platinum ($Pt^0$), in a supported form or as such, can be added into the reaction medium of the invention's process in a large range of concentrations. As non-limiting examples, one can cite as metal concentration values those ranging from 1 ppm to 20000 ppm, relative to the total amount of substrate. Preferably, the metal concentration will be comprised between 5 ppm to 7000 ppm, or even between 5 ppm and 100 or 1000 ppm. It goes without saying that the optimum concentration of metal will depend, as the person skilled in the art knows, on the nature of the latter, on the nature of the substrate, if the process is run in batch or continuously, on the temperature and on the pressure of $H_2$ used during the process, as well as the desired time of reaction.

The process according to the invention is carried out in the presence of molecular hydrogen or hydrogen source.

According to any one of the above embodiments of the invention, said hydrogen source can be a transfer hydrogenation agent. Specific and non limiting examples of catalytic transfer hydrogenation agents are tetralin, formic acid, limonene, cyclohexanol.

The transfer hydrogen agent can be added into the reaction medium of the invention's process in a large range of concentrations. As non-limiting examples, one can cite as hydrogen source concentration values those ranging from 0.5% to 100% w/w, or even between 40% to 70% w/w, relative to the amount of compound of formula (II). A large amount of transfer hydrogenation agent is used as only a small part generates molecular hydrogen. For instance, approximately around 10% of tetralin are converted into molecular hydrogen. It goes without saying that the optimum concentration of hydrogen source will depend, as the person skilled in the art knows, on the nature of the latter, on the nature of the substrate, of the temperature and on the catalyst used during the process, as well as the desired time of reaction.

According to any one of the above embodiments of the invention, as an alternative to the transfer hydrogenation agent, the molecular hydrogen can be used pure or mixed with an inert gas. Specific and non limiting examples of such inert gas are nitrogen or argon. The $H_2$/inert gas volume ratio is comprised between 1/1 to 0.01/1 and more preferably the ratio is 0.05/1.

The molecular hydrogen can be added into the reaction medium of the invention's process in a large range of concentrations. As non-limiting examples, one can cite as molecular hydrogen concentration values those ranging from 1 mol % to 100 mol %, relative to the amount of compound of formula (II). Preferably, the hydrogen source concentration will be comprised between 3 mol % to 75 mol % relative to the amount of compound of formula (II). Of course, a person skilled in the art is well able to adjust the pressure or the flow (e.g. in a continuous process) of molecular hydrogen to obtain this range of concentration as a function of the process is batch or continuous. The person skilled in the art is also well able to adjust the concentration of molecular hydrogen as a function of the catalyst load and of dilution of the substrate in the solvent.

The invention's process can be carried out under batch or continuous conditions. According to a particular embodiment of the invention, the process is a continuous one, as it allows higher productivity.

The reaction can be carried out in the presence or absence of a solvent. When a solvent is required or used for practical reasons, then any solvent current in such reaction type can be used for the purposes of the invention. Non-limiting examples include $C_{6-12}$ aromatic solvents such as toluene or 1,3-diisopropylbenzene or cumene or pseudocumene or benzyl acetate or xylene, $C_{3-16}$ alkane such as hexadecane, or mixtures thereof. The choice of the solvent is a function of the nature of the substrate and of the complex and the person skilled in the art is well able to select the solvent most convenient in each case to optimize the reaction.

The temperature at which the isomerisation can be carried out is comprised between 120° C. and 300° C. More preferably in the range of between 170° C. and 250° C. for a continuous process and between 170° C. to 185° C. for a batch process. Of course, a person skilled in the art is also able to select the preferred temperature as a function of the melting and boiling point of the starting and final products as well as the desired time of reaction or conversion.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in $CDCl_3$ with a 360 MHz or 100 MHz machine for $^1H$ or $^{13}C$ respectively, the chemical displacements δ are indicated in ppm with respect to TMS as standard, the coupling constants J are expressed in Hz.

General Procedure

Example 1

Catalytic isomerisation of 3-methyl-2-methylenebutanal using Pd/C

4% Palladium on carbon (4 g) was charged in a tubular reactor and heated to 170° C. under stream of $N_2$. The reactor was purged with $N_2$ gas for 4 hrs followed by addition of the 3-methyl-2-methylenebutanal (3800 g) at a rate of 0.23 g/min and $H_2/N_2$ gas (0.05:1 vol/vol) at a rate of 200 mL/min ($H_2$ gas 42 mol % relative to substrate). Said conditions allowed a LHSV (Liquid Hourly Space Velocity=[Reactant Liquid Flow Rate]/[Reactor Volume-catalyst volume]) of 4.28 $h^{-1}$.

Product was collected under $N_2$ and redistilled under reduced pressure afforded 2,3-dimethylbut-2-enal (2065 g, 54% yield).

Example 2

Catalytic isomerisation of 2-methylenepent-4-enal using Pd/C

4% Palladium on carbon (4 g) was charged in a tubular reactor and heated to 170° C. under stream of $N_2$. The reactor was purged with $N_2$ gas for 4 hrs followed by addition of the 2-methylenpent-4-enal (100 g) in diisopropyl benzene (100 g) at a rate of 0.2 g/min and $H_2/N_2$ gas (0.05:1 vol/vol) at a rate of 200 mL/min ($H_2$ gas 75 mol % relative to substrate). 2-Methylpent-2,4-dienal was collected under $N_2$ and yields were determined by GC internal standard method (25 g, 25% yield).

Example 3

Catalytic isomerisation of 3-methyl-2-methylenebutanal using Pd/C and various hydrogen sources 4% Palladium on carbon (10 g) was charged in a tubular reactor and heated to 180° C. under gentle stream of $N_2$. The reactor was purged with $N_2$ gas for 18 hrs followed by addition of the 3-methyl-2-methylenebutanal and hydrogen source (table 1, wt/wt %) at a rate of 0.25 g/min and 20 mL/min $N_2$ gas. Product was collected under $N_2$ and yields were determined by GC internal standard method. Under these conditions several transfer hydrogenation agents were tested, as reported in Table 1.

TABLE 1

Isomerisation of 3-methyl-2-methylenebutanal with Pd/C complex and various transfer hydrogenation agents

| Test | Hydrogen source | Transfer hydrogenation agent to substrate (w/w %) | Yields (%) |
|---|---|---|---|
| 1 | Tetralin | 50 | 83 |
| 2 | Formic acid | 10 | 55 |
| 3 | Limonene | 50 | 72 |
| 4 | Cyclohexanol | 50 | 40 |

Example 4

Catalytic isomerisation of 6-ethylidene-2,2-dimethylcyclohexan-1-one using Pd/C and hydrogen source 5% Palladium on carbon (11 g), 6-ethylidene-2,2-dimethylcyclohexan-1-one (415 g) and pseudocumene (390 g) were charged in a reactor. The reactor was purged with $N_2$ gas. The reaction mixture was heated to 170° C. and acid formic (3 g) was added over 15 h. The reactor was cool down. The reaction mixture was filtrated and distilled under reduced pressure afforded 2-ethyl-6,6-dimethylcyclohex-2-en-1-one (394 g, 93% yield).

Example 5

Catalytic isomerisation of E/Z 6-ethylidene-2,2-dimethyl-1-cyclohexanone using Pd/C and molecular hydrogen 4% Palladium on carbon (4 g) is charged in a tubular reactor and heated to 150° C. under stream of $N_2$. The reactor is purged with $N_2$ gas for 24 hrs and then heated to 190° C. followed by addition of the 6-ethylidene-2,2-dimethyl-1-cyclohexanone (88 g) at a rate of 0.26 g/min and $H_2/N_2$ gas (0.05:1 vol/vol) at a rate of 100 mL/min (molar ratio of $H_2$ gas:substrate=13% mol/mol). Said conditions allowed a LHSV (Liquid Hourly Space Velocity=[Reactant Liquid Flow Rate]/[Reactor Volume-catalyst volume]) of 4.7 $h^{-1}$. Product is collected under $N_2$ and redistilled under reduced pressure afforded 2-ethyl-6,6-dimethylcyclohex-2-enone (71 g, 81% yield).

What is claimed is:

1. A process for the preparation of a compound of formula (I)

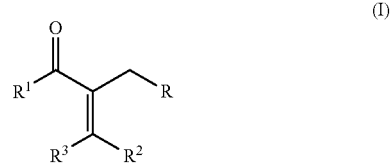

wherein R, $R^1$ and $R^2$, simultaneously or independently, represent a hydrogen atom or a linear or branched $C_{1-5}$ alkyl group; $R^3$ represents a linear or branched $C_{1-5}$ alkyl or alkenyl group;
by the isomerisation of the corresponding compound of the formula (II)

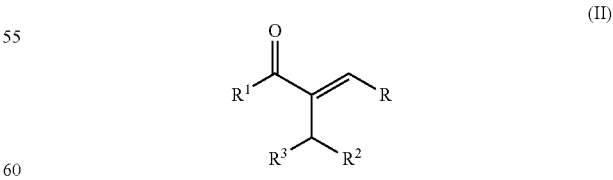

wherein R, $R^1$, $R^2$ and $R^3$ have the same meaning as in formula (I);
said isomerization being performed in the presence of molecular hydrogen or a hydrogen source, and a catalyst system comprising a metal selected from palladium (Pd) or platinum (Pt).

2. A process according to claim 1, characterized in that said $R^1$ represents a hydrogen atom.

3. A process according to claim 1, characterized in that said $R^2$ represents a $C_{1-5}$ alkyl group and said R represents a hydrogen atom.

4. A process according to claim 1, characterized in that said compound of formula (I) is 2,3-dimethylbut-2-enal or 2-methylpenta-2,4-dienal.

5. A process according to claim 1, characterized in that said metal is supported on carbon or aluminum oxide.

6. A process according to claim 5, characterized in that said hydrogen source is tetralin, formic acid, limonene or cyclohexanol.

7. A process according to claim 1, characterized in that said molecular hydrogen is mixed with nitrogen or argon in a volume ratio comprised between 1/1 to 0.01/1.

8. A process according to claim 1, characterized in that said process is a continuous process.

9. A process for the preparation of a compound of formula (I)

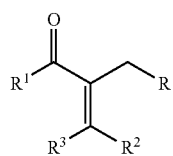

(I)

wherein R, $R^1$ and $R^2$, simultaneously or independently, represent a hydrogen atom or a linear or branched $C_{1-5}$ alkyl group; $R^3$ represents a linear or branched $C_{1-5}$ alkyl or alkenyl group which consists of the isomerisation of the corresponding compound of the formula (II)

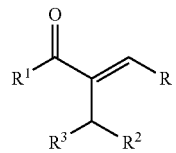

(II)

wherein R, $R^1$, $R^2$ and $R^3$ have the same meaning as in formula (I) in the presence of a catalyst system of metal selected amongst palladium (Pd) or platinum (Pt); and molecular hydrogen or a hydrogen source.

10. A process according to claim 9, characterized in that said $R^1$ represents a hydrogen atom.

11. A process according to claim 9, characterized in that said $R^2$ represents a $C_{1-5}$ alkyl group and said R represents a hydrogen atom.

12. A process according to claim 9, characterized in that said compound of formula (I) is 2,3-dimethylbut-2-enal or 2-methylpenta-2,4-dienal.

13. A process according to claim 9, characterized in that said metal is supported on carbon or aluminum oxide.

14. A process according to claim 13, characterized in that said hydrogen source is tetralin, formic acid, limonene or cyclohexanol.

15. A process according to claim 9, characterized in that said molecular hydrogen is mixed with nitrogen or argon in a volume ratio comprised between 1/1 to 0.01/1.

16. A process according to claim 9, characterized in that said process is a continuous process.

\* \* \* \* \*